United States Patent
Kim et al.

(10) Patent No.: US 8,050,488 B2
(45) Date of Patent: Nov. 1, 2011

(54) METHOD OF ANALYZING A WAFER SAMPLE

(75) Inventors: Jong-An Kim, Seoul (KR); Yu-Sin Yang, Seoul (KR); Chung-Sam Jun, Suwon-si (KR); Moon-Shik Kang, Yongin-si (KR); Ji-Hye Kim, Anyang-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 906 days.

(21) Appl. No.: 12/041,127

(22) Filed: Mar. 3, 2008

(65) Prior Publication Data

US 2008/0219547 A1    Sep. 11, 2008

(30) Foreign Application Priority Data

Mar. 9, 2007   (KR) .................. 10-2007-0023253

(51) Int. Cl.
*G06K 9/00* (2006.01)
(52) U.S. Cl. .......... 382/141; 382/152; 348/86; 348/125; 700/95
(58) Field of Classification Search .......... 382/141–152; 348/86–95, 125–134; 700/95–212
See application file for complete search history.

(56) References Cited

U.S. PATENT DOCUMENTS

| 5,991,699 | A  | * | 11/1999 | Kulkarni et al. | ............... | 702/83 |
| 6,842,245 | B2 |   | 1/2005  | Ando            |                 |        |
| 7,570,796 | B2 | * | 8/2009  | Zafar et al.    | ................ | 382/144 |
| 2004/0091142 | A1 | * | 5/2004 | Peterson et al. | ............. | 382/144 |

FOREIGN PATENT DOCUMENTS

| JP | 2000-113189 | 4/2000 |
| JP | 2004-177139 | 6/2004 |

* cited by examiner

*Primary Examiner* — Wesley Tucker
(74) *Attorney, Agent, or Firm* — F.Chau & Associates, LLC (57) ABSTRACT

In a method of analyzing a wafer sample, a first defect of a photoresist pattern on the wafer sample having shot regions exposed with related exposure conditions is detected. A first portion of the pattern includes the shot regions exposed with an exposure condition corresponding to a reference exposure condition and a tolerance error range of the reference exposure condition. The first defect repeatedly existing in at least two of the shot regions in a second portion of the pattern is set up as a second defect of the pattern. A first reference image displaying the second defect is obtained. The first defect of the shot regions in the first portion corresponding to the second defect is set up as a third defect corresponding to weak points of the pattern. The exposure conditions of the shot region having no weak points are set up as an exposure margin of an exposure process.

12 Claims, 4 Drawing Sheets

METHOD OF ANALYZING A WAFER SAMPLE

CROSS-REFERENCE TO RELATED APPLICATION

This application claims priority under 35 U.S.C. §119 to Korean Patent Application No. 2007-23253, filed on Mar. 9, 2007, the contents of which are herein incorporated by reference in their entireties.

BACKGROUND OF THE INVENTION

1. Technical Field

Example embodiments of the present invention relate to a method of analyzing a wafer sample. More particularly, example embodiments of the present invention relate to a method of analyzing a wafer sample for detecting a weak point of a pattern in an exposure process to set up a desired margin of the exposure process.

2. Discussion of Related Art

Semiconductor devices are generally manufactured through repeatedly performing separate processes that include a deposition process for forming a layer on a substrate, a chemical mechanical polishing (CMP) process for planarizing the layer, a photo process for forming a photoresist pattern on the layer, an etching process for patterning the layer into a pattern having electrical characteristics using the photoresist pattern, an ion implantation process for implanting ions into predetermined portions of the substrate, a cleaning process for removing particles from the substrate, an inspection process for inspecting defects of the layer and the pattern, and the like.

As a design rule of the semiconductor device decreases, a margin of an exposure process in the photo process also decreases and a step of detecting a weak point of a photoresist pattern becomes more important. In the conventional method of analyzing a wafer sample, the photoresist pattern is prepared on the wafer sample having a plurality of shot regions where patterns are repeatedly transcribed, and then the wafer sample is inspected with a high precision to detect defects of the photoresist pattern. The defects of the photoresist pattern repeatedly detected relative to each shot region are considered as the weak points of the photoresist pattern, and then the margin of the exposure process is adjusted in accordance with the number of the detected weak points of the photoresist pattern.

With a determination reference obtained from the repeatedly detected defects of the photoresist pattern, the number of weak points and the margin of the exposure process are changed. The determination reference, however, may unfortunately vary in accordance with the users. Although the weak points of the photoresist pattern and the margin of the exposure process are analyzed by one user, a consistent determination reference of analysis may not be ensured because the user subjectively determines the determination reference. Furthermore, the step of detecting the weak points of the photoresist pattern and a step of ensuring the margin of the exposure process may not be automatically carried out because of the subjective determination of the user.

SUMMARY OF THE INVENTION

Example embodiments of the present invention provide methods of analyzing a wafer sample to ensure a reproducibility of detecting weak points of a photoresist pattern and sufficiently ensuring a margin of an exposure process by reducing a subjective determination of the user.

According to an example embodiment of the present invention, there is provided a method of analyzing a wafer sample. In the method of analyzing the wafer sample, a first defect of a photoresist pattern on the wafer sample is detected. The wafer sample has a plurality of shot regions exposed with related exposure conditions, respectively. The shot regions are set up in a first portion of the photoresist pattern and a second portion of the photoresist pattern. The first portion including the shot regions is exposed with exposure conditions corresponding to a reference exposure condition and a tolerance error range of the reference exposure condition. A first defect repeatedly detected in at least two of the shot regions of the second portion is set up as a second defect of the photoresist pattern. A first reference image displaying the second defect is obtained, and then a position of the shot regions in the first portion corresponded to the second defect is set up as a third defect of the photoresist pattern. The third defect is set up as the weak points of the photoresist pattern.

In example embodiments, the exposure conditions relative to a shot region having no weak points may be additionally set up as an exposure margin of the exposure process. It may be determined whether the reference exposure condition belongs to the exposure margin of the exposure process. Then, the weak points of the shot region of the first portion may be displayed in a second reference image when the reference exposure condition belongs to the exposure margin of the exposure process.

In an example embodiment, a central value of a predetermined range of the exposure condition may be set up as a new reference exposure margin when the reference exposure condition does not belong to the exposure margin. Then, the wafer sample may be analyzed again using the new reference exposure margin.

In an example embodiment, the weak points of the photoresist pattern may be reviewed to identify whether the weak points correspond to actual weak points before setting up the exposure conditions of the shot region having no weak points as the exposure margin of the exposure process. The weak points may be reviewed using a scanning electron microscope.

In an example embodiment, the weak points caused by an optical proximity correction may be set up using the weak points in each of the shot regions of the first portion when the reference exposure condition belongs to the exposure margin of the exposure process. In setting up the weak points caused by the optical proximity correction, each of the shot regions of the first portion may be divided into a plurality of die regions. The weak points that repeatedly existed in at least two of the die regions in each of the shot regions may be detected.

In example embodiments, the exposure condition may include at lease two conditions selected from a group consisting of an exposure time, a focal distance and an exposure intensity.

In detecting the first defect according to example embodiments, the wafer sample may be prepared to have a reference shot region formed by transcribing a predetermined pattern with a reference exposure condition and a peripheral shot region formed by transcribing the predetermined pattern while varying the exposure conditions of the exposure process. A reference inspection precision may be set up using the wafer sample, and then the wafer sample may be inspected with the reference inspection precision.

In setting up the reference inspection precision according to example embodiments, the wafer sample may be divided into a first region having relatively many defects and a second region having relatively few defects. The defects of the wafer sample may be detected by gradually varying an inspection precision. A defect number ratio between the number of defects in the first region and the number of defects in the second region may be determined in accordance with the inspection precision. The reference inspection precision may be selected within a range in which the defect number ratio increases.

In an example embodiment, the reference inspection precision may be selected by subtracting a minimum value of the defect number ratio from a maximum value of the defect number ratio within the range in which the defect number ratio increases to obtain a difference between the maximum value and the minimum value, by adding a previously set value of the difference between the maximum value and the minimum value into the minimum value of the defect number ratio, to obtain a sum of the minimum value and the previously set value of the difference, and by obtaining the inspection precision corresponding to the sum of the defect number ratio so as to set up the inspection precision as the reference inspection precision.

In an example embodiment, the reference inspection precision may be selected by multiplying a difference between inspection precision values by a previously set inspection precision value to obtain an offset value of a previously set inspection precision, and by subtracting the offset value from the inspection precision value corresponding to the maximum value of the defect number ratio to obtain the reference inspection precision.

In an example embodiment, the reference inspection precision may be selected by obtaining a previously set defect number ratio considering characteristics of the wafer sample, by dividing the wafer sample into a first region having relatively many defects and a second region having relatively few defects, by detecting the defects of the wafer sample by gradually varying the inspection precision, by determining a difference between the number of defects in the first region and the number of defects in the second region in accordance with the inspection precision, and by selecting the reference inspection precision from the inspection precision within a range in which the defect number ratio increases.

According to example embodiments of the present invention, defects of a reference shot region and a shot region adjacent the reference shot region and defects of a shot region separated from the reference shot region may be detected to easily detect weak points of a pattern provided on a wafer sample, and to easily set up a margin of an exposure process.

BRIEF DESCRIPTION OF THE DRAWINGS

Example embodiments of the present invention will be understood in more detail from the following descriptions taken in conjunction with the accompanying drawings, in which.

DETAILED DESCRIPTION OF EXAMPLE EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those of ordinary skill in the art.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Figure 1:
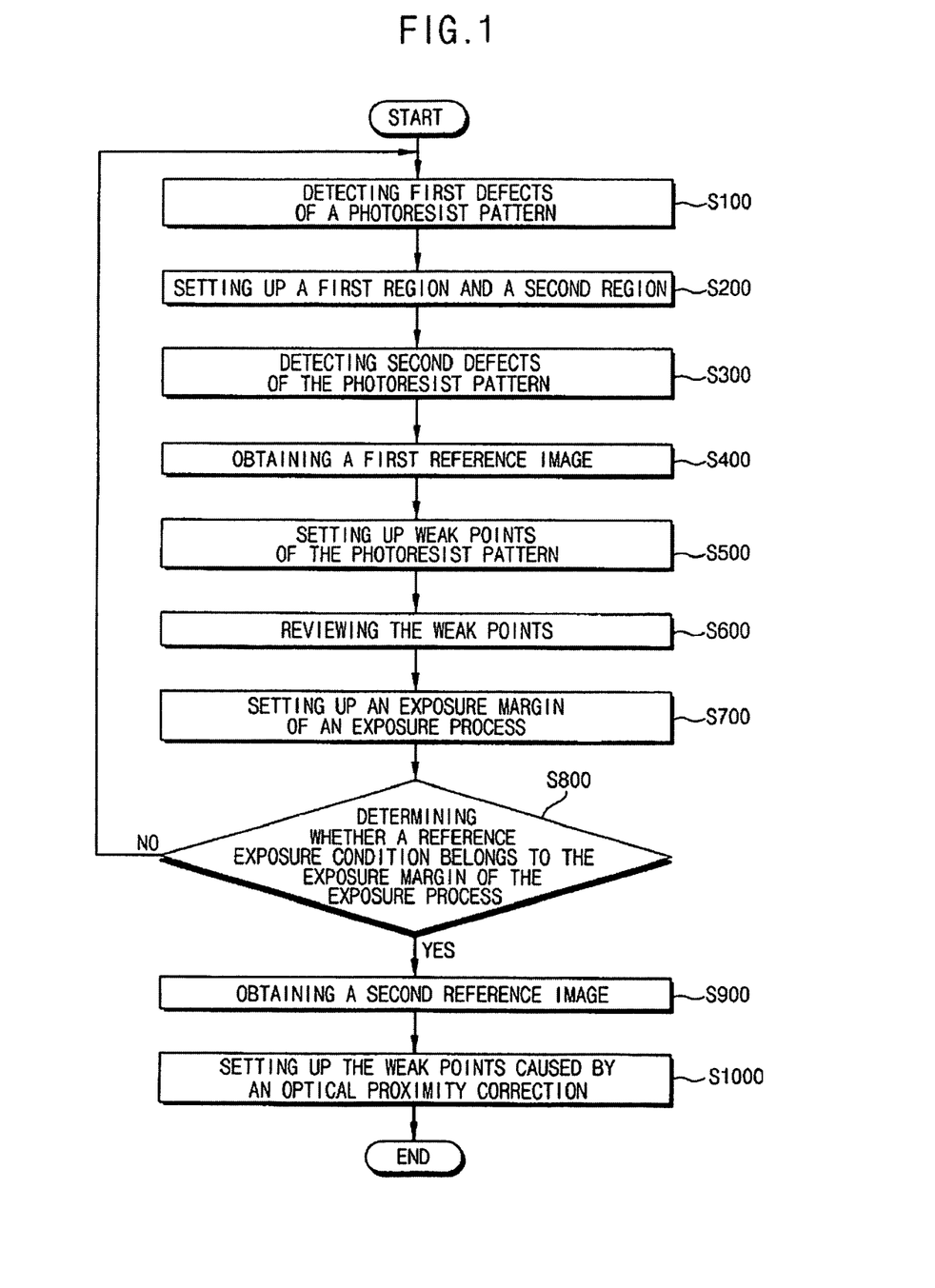
FIG. 1 is a block diagram illustrating a method of analyzing a wafer sample in accordance with an example embodiment of the present invention.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. FIG. 1 is a block diagram illustrating a method of analyzing a wafer sample in accordance with an example embodiment of the present invention.

Referring to FIG. 1, first defects of a photoresist pattern provided on the wafer sample are detected in step S100. The photoresist pattern may be formed on the wafer sample through a coating process, an exposure process and a developing process.

A step of detecting the first defect of the photoresist pattern according to an example embodiment will be described in detail.

Figure 2:
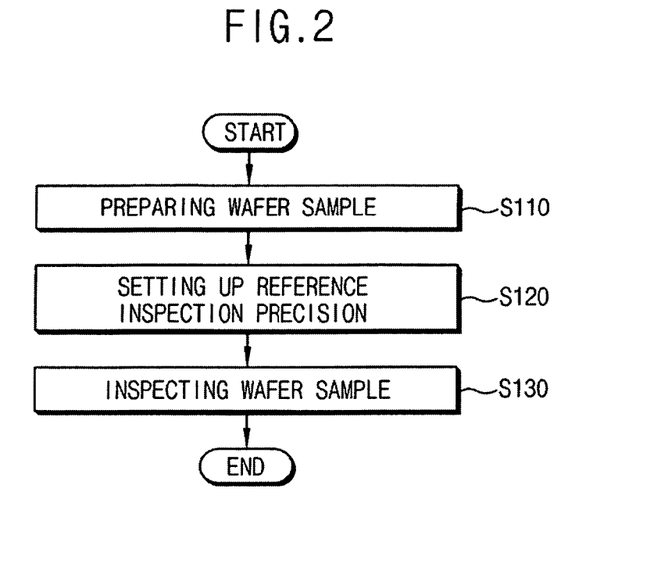
FIG. 2 is a block diagram illustrating a step of detecting the first defect of the photoresist pattern in accordance with an example embodiment of the present invention.
Figure 3:
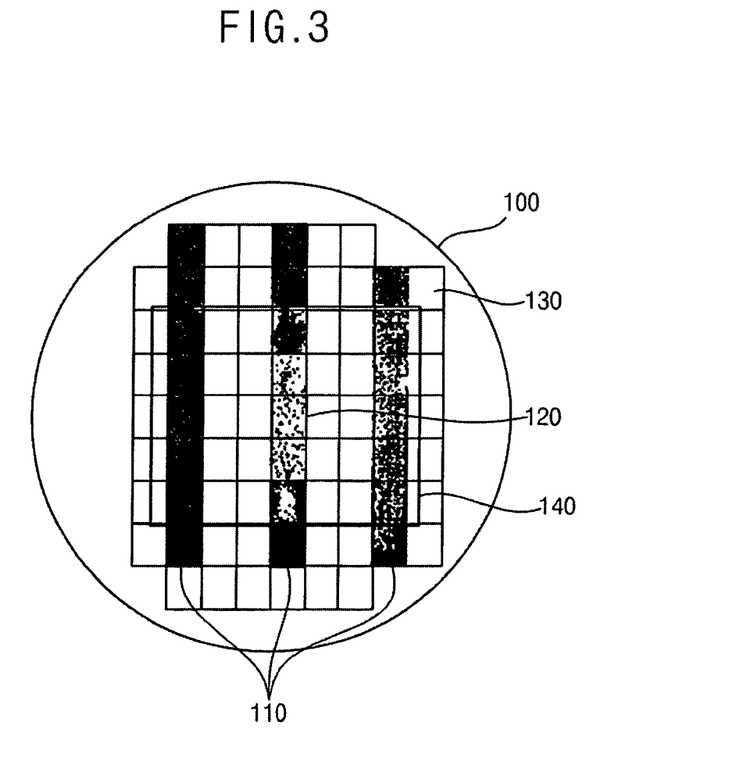
FIG. 3 is a plan view illustrating a wafer sample in accordance with an example embodiment of the present invention.

FIG. 2 is a block diagram illustrating the step of detecting the first defects of the photoresist pattern in accordance with an example embodiment of the present invention. FIG. 3 is a plan view illustrating the wafer sample in accordance with an example embodiment of the present invention.

Referring to FIGS. 1 and 2, the wafer sample is prepared in step S110. The photoresist pattern possibly having the first defect is formed on the wafer sample.

Referring to FIGS. 2 and 3, a wafer sample 100 includes a plurality of shot regions 110. In the shot regions 110, a reference shot region 120 may be formed by transcribing a predetermined pattern to the photoresist pattern with a reference exposure condition in the exposure process. The reference shot region 120 may be positioned at a central portion of the wafer sample 100. A peripheral shot region of the shot regions 110 may be formed by transcribing the predetermined pattern to the photoresist pattern while varying exposure conditions in the exposure process. In an example embodiment, the shot regions 110 may have line shapes separated from each other by a predetermined interval. In this example embodiment, unexposed regions of the photoresist pattern may be located between adjacent shot regions 110.

In an example embodiment, the exposure conditions of the exposure process may include at least two of an exposure time, a focal distance and an exposure intensity. When two exposure conditions are selected from among the exposure time, the focal distance, and the exposure intensity, the non-selected one may be constantly maintained in the exposure process. For example, when the exposure conditions include the exposure time and the exposure intensity, the focal distance may not vary in the exposure process.

In step S120, a reference inspection precision is set up using the wafer sample 100 having the photoresist pattern formed thereon.

A step of setting up the reference inspection precision according to an example embodiment will be described in detail.

Figure 4:
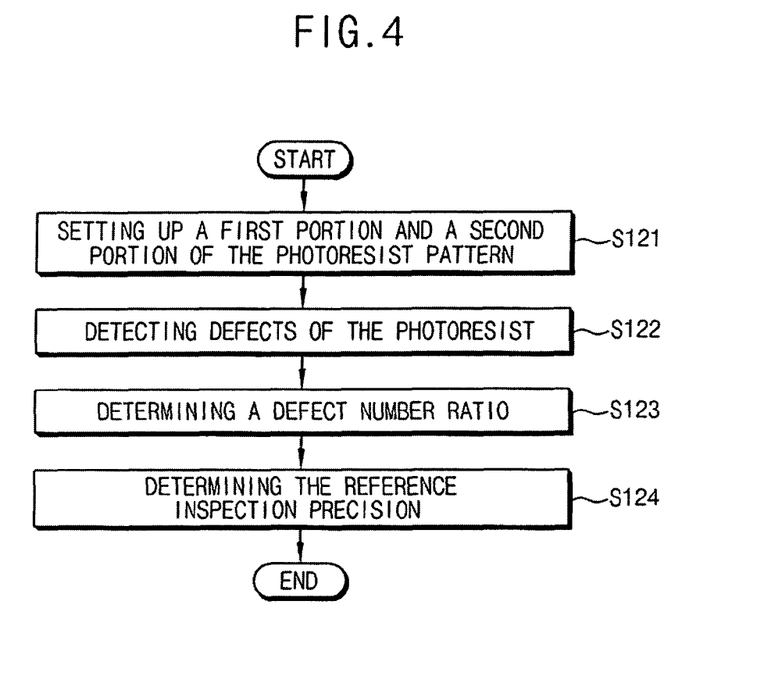
FIG. 4 is a block diagram illustrating a step of setting up a reference inspection precision in accordance with an example embodiment of the present invention.

FIG. 4 is a block diagram illustrating the step of setting up the reference inspection precision in accordance with an example embodiment of the present invention.

Referring to FIGS. 2 to 4, the photoresist pattern on the wafer sample 100 is divided into a first portion 130 and a second portion 140 in step S121. That is, the first and the second portions 130 and 140 of the photoresist pattern are set up in step S121.

In example embodiments, the first portion 130 of the photoresist pattern may include relatively many defects whereas the second portion 140 of the photoresist pattern may include relatively few defects. In the exposure process, the number of defects may increase as a difference between the exposure conditions and reference exposure conditions increases. Thus, the first portion 130 may include some of the shot regions 110 separated from the reference shot region 120. Meanwhile, the number of defects may be reduced as the difference between the exposure conditions and the reference exposure conditions is decreased. Hence, the second portion 140 may include the reference shot region 120 and other shot regions 110 adjacent the reference shot region 120.

In step S122, the defects of the photoresist patterns are detected by gradually varying the inspection precision.

In step S123, a defect number ratio (N1/N2) between the first number of the defects (N1) in the first portion 130 and the second number of the defects (N2) in the second portion 140 is determined in accordance with the inspection precision. Namely, the defect number ratio (N1/N2) of the first and the second portion 130 and 140 may be calculated in step S123.

Figure 5:
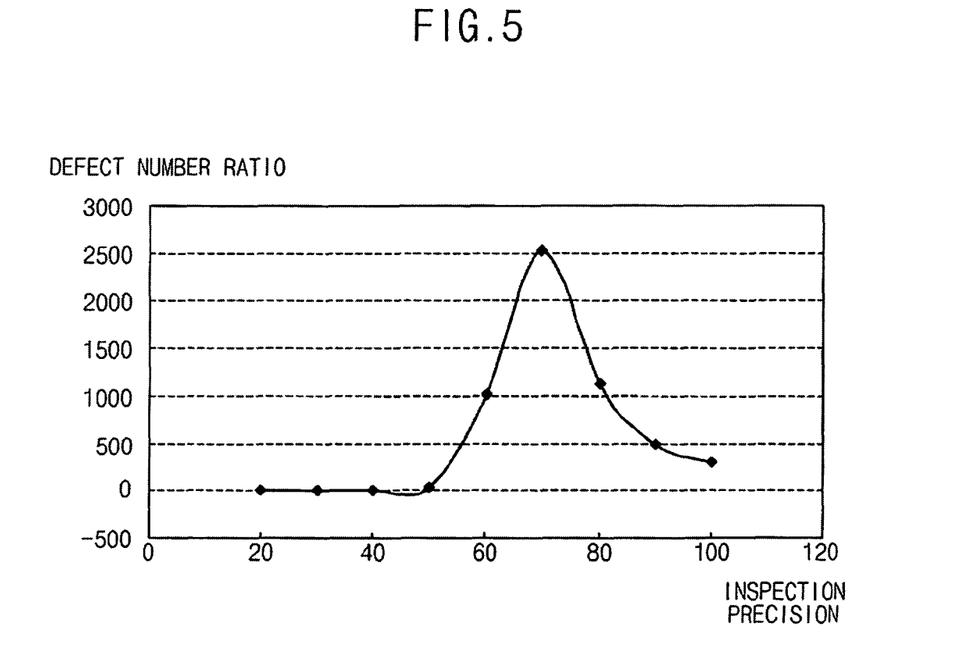
FIG. 5 is a graph illustrating a defect number ratio relative to an inspection precision in accordance with an example embodiment of the present invention.

When the inspection precision is changed, the first number of defects (N1) in the first portion 130 and the second number of defects (N2) in the second portion 140 are also changed. The defect number ratio (N1/N2) may be determined in the first and the second portions 130 and 140 with respect to related respective inspection precisions. The defect number ratios (N1/N2) relative to the related inspection precisions are illustrated in FIG. 5.

In step S124, the reference inspection precision is determined in a range of the inspection precision in which the defect number ratio (N1/N2) is increased considering characteristics of the wafer sample 100.

In an example embodiment, a minimum value of the defect number ratio (N1/N2) is subtracted from a maximum value of the defect number ratio (N1/N2) in the range in which the defect number ratio (N1/N2) is increased so as to obtain a first difference between the maximum value and the minimum value. A previously set value of the first difference is added to the minimum value of the defect number ratio (N1/N2) to obtain a first sum of the minimum value and the previously set value of the first difference. The previously set value may be determined in accordance with the type of layer formed on the wafer sample 100 and a shape of the photoresist pattern on the wafer sample 100. When the inspection precision corresponding to the first sum of the minimum value and the previously set value of the first difference based on the defect number ratio (N1/N2) is obtained, the reference inspection precision may be determined from the corresponding inspection precision.

In an example embodiment, the previously set value of the first difference between the maximum value and the minimum value may be subtracted from the maximum value of the defect number ratio (N1/N2) so as to obtain a second difference of the defect number ratio (N1/N2). When the inspection precision corresponding to the second difference of the defect number ratio (N1/N2) is obtained, the reference inspection precision may be determined from the corresponding inspection precision.

In an example embodiment, about ninety percent of the first difference between the maximum value and the minimum value may be added to the minimum value of the defect number ratio (N1/N2) so as to obtain a corrected maximum value of the defect number ratio (N1/N2). About ten percent of the first difference between the maximum value and the minimum value may be added to the minimum value of the defect number ratio (N1/N2), so as to obtain a corrected minimum value of the defect number ratio (N1/N2). The corrected minimum value of the defect number ratio (N1/N2) may be subtracted from the corrected maximum value of the defect number ratio (N1/N2) to thereby obtain a third difference between the corrected maximum value and the corrected minimum value. A previously set value of the third difference between the corrected maximum value and the corrected minimum value may be added to the corrected minimum value of the defect number ratio (N1/N2) in order to obtain a second sum of the corrected minimum value and the previously set value of the third difference between the corrected maximum and the corrected minimum value. When the inspection precision corresponding to the second sum of the defect number ratio (N1/N2) is obtained, the reference inspection precision may be determined from the corresponding inspection precision.

In an example embodiment, a first inspection precision value corresponding to the maximum value of the defect number ratio (N1/N2) in the range in which the defect number ratio (N1/N2) is increased may be obtained. Additionally, a second inspection value corresponding to the minimum value of the defect number ratio (N1/N2) in the range may be obtained. Then, the second inspection precision value corresponding to the minimum value of the defect number ratio (N1/N2) may be subtracted from the first inspection precision value corresponding to the maximum value of the defect number ratio (N1/N2) so as to obtain a difference between the first inspection precision value and the second inspection value. The difference of the inspection precision values may be multiplied by a previously set value to obtain an offset value of a previously set inspection precision. The previously set value may vary in accordance with the kind of a layer formed on the wafer sample 100 and a shape of the photoresist pattern on the wafer sample 100. The offset value may be subtracted from the first inspection precision value corresponding to the maximum value of the defect number ratio (N1/N2) in order to determine the reference inspection precision.

In an example embodiment, about ninety percent of the first difference of the maximum value and the minimum value may be added to the minimum value of the defect number ratio (N1/N2) to obtain a corrected maximum value of the defect number ratio (N1/N2). Additionally, about ten percent of the first difference of the maximum value and the minimum value may be added to the minimum value of the defect number ratio (N1/N2) to obtain a corrected minimum value of the defect number ratio (N1/N2). There may be obtained the first and the second inspection precision values corresponding to the corrected maximum and the corrected minimum values of the defect number ratio (N1/N2) in the range in which the defect number ratio (N1/N2) increases. The second inspection precision value corresponding to the corrected minimum value of the defect number ratio (N1/N2) may be subtracted from the first inspection precision value corresponding to the corrected maximum value of the defect number ratio (N1/N2) in order to obtain the difference between the first and the second inspection precision values. The difference of the inspection precision values may be multiplied by the previously set value so as to obtain the offset value of the previously set inspection precision.

Referring now to FIGS. 2 to 4, after the reference inspection precision is determined as described above, the photoresist pattern on the wafer sample 100 is inspected with the reference inspection precision so as to detect the first defects of the photoresist pattern in step SI 30.

In an example embodiment, the inspection step of detecting the first defects of the photoresist pattern may be performed relative to each of the shot regions 110 of the wafer sample 100. For example, an image of one of the shot regions 110 and images of unexposed regions adjacent one of the shot regions 110 may be compared to detect the first defects of the photoresist pattern.

Referring to FIGS. 1 to 4, in step S200, a first region and a second region are set up among the shot regions 110 of the wafer sample 100. The first region may include the shot region 110 that meets a tolerance error range of the reference exposure condition in the exposure process. The second region may include other shot regions 110 except for the first region.

When the exposure process is executed with the reference exposure condition, an error of the reference exposure condition may occur because of some other factors. For example, an error may occur in the exposure time, the focal distance, and/or the exposure intensity. In this example embodiment, the first region may include the shot region 110 exposed under an exposure condition with the tolerance error range of the reference exposure condition. The, the second region, however, may include the shot regions 110 exposed under an exposure condition deviated from the tolerance error range of the reference exposure condition.

In step S300, second defects of the photoresist pattern are detected from among the first defects. The second defects may be repeated in at least two of the shot regions 110 included in the second region.

In an example embodiment, the shot regions 110 of the second region may have the first defects, respectively. When the first defects have predetermined positions in at least two of the shot regions 110 of the second region, the first defects may be set up as the second defects of the photoresist pattern.

In step S400, a first reference image displaying the second defects is obtained. In an example embodiment, the first reference image may have a size substantially the same as the size of each of the shot regions 110. The second defects displayed in the first reference image may be located at positions of the shot regions 110 where the second defects of the photoresist pattern are actually located.

Although the first reference image displaying the second defects is obtained after detecting the second defects, the first defects of the shot regions 110 included in the second region may be displayed, and then the first reference image may be obtained by displaying the second defects at least twice overlapped among the first defects.

In step S500, positions of third defects of the photoresist pattern are set up as the weak points of the photoresist pattern. That is, the weak points of the photoresist pattern are set up in step S500. The third defects may be selected from among the second defects corresponding to the second defects displayed in the first reference image.

In an example embodiment, the shot regions 110 of the first region may be compared with the first reference image. The third defects of the photoresist pattern may be obtained by selecting the second defects that correspond to the second defects of the first reference image among the first defects of the shot regions 110 in the first region. The third defects may be set up as the weak points of the photoresist pattern. The weak points of the photoresist pattern may mainly occur as a thinning, a bridge and/or a cutting, which are generated in a step of transcribing the pattern onto the photoresist pattern. Since the exposure conditions relative to the shot regions 110 may be substantially different, the weak points of the photoresist pattern may be advantageously identified in accordance with the exposure conditions, respectively.

In step S600, the weak points of the photoresist pattern are reviewed to confirm whether the weak points actually occur or not.

In an example embodiment, the weak points of the photoresist pattern may be obtained by optically analyzing the third defects of the photoresist pattern. Because an optical analysis for the third defects may have an error, some of the weak points may not correspond to actual weak points. Therefore, the weak points in the shot regions 110 of the first region should be reviewed to ensure the actual weak points of the photoresist pattern. This review step may be performed using a scanning electron microscope (SEM).

In step S700, the exposure conditions relative to the shot regions 110 having no weak points are set up as an exposure margin of the exposure process.

When the shot regions 110 having no weak points exist among the shot regions 110 of the first region, the exposure margin, corresponding to the tolerance error range of the exposure condition, may be obtained using the exposure condition with respect to the shot regions 110 having no weak points. When only one shot region 110 having no weak points exists, the exposure condition may be obtained. Further, when two shot regions 110 having no weak points exist, the exposure margin of the exposure process may be obtained. The exposure condition or the exposure margin may be selected from the tolerance error range of the exposure condition to thereby prevent the weak points of the photoresist pattern caused in the exposure process.

When any shot regions 110 having no weak points among the shot regions 110 of the first regions do not exist, the exposure condition or the exposure margin may not be obtained. In other words, the exposure condition or the exposure margin may not be obtained within the tolerance error range of the exposure condition to prevent the weak points of the photoresist pattern. In this example embodiment, after an exposure mask having a pattern may be corrected to perform the exposure process, a new wafer sample may be prepared using the corrected mask. Then, the new wafer sample may be inspected as described above.

In step S800, it is determined whether the reference exposure condition belongs to the exposure margin of the exposure process.

In an example embodiment, the reference exposure condition may be compared to the exposure margin, or the reference shot region 120 may be compared with the shot regions 110 having no weak points among the shot regions 110 in the first region.

When the reference exposure condition does not belong to the exposure margin of the exposure process, the reference shot region 120 where the pattern of the mask is repeatedly transcribed with the reference condition may have the weak points of the photoresist pattern. Because the weak points may not exist in the reference shot region 120 where the pattern of the mask is repeatedly transcribed, the reference exposure condition may be erroneously obtained. Hence, the reference exposure condition may be obtained again using the exposure margin of the exposure process. When the exposure margin of the exposure process has various values within a predetermined range, a central value in the range of the exposure condition may be set up again as the reference exposure condition. When the exposure margin of the exposure process corresponds to one exposure condition, this exposure condition may be set up again as the reference exposure condition. After a new wafer sample may be prepared using the reference exposure condition set up again, the new wafer sample may be analyzed again.

In step 900, when the reference exposure condition belongs to the exposure margin of the exposure process, the weak points in the shot regions 110 of the first portion 130 is displayed as a second reference image.

When the reference exposure condition belongs to the exposure margin, the reference shot region 120 where the pattern of the mask is repeatedly transcribed with the reference condition may not have the weak points. The weak points of the shot regions 110 of the first portion 130 may be displayed in the second reference image that has a size substantially the same as those of the shot regions 110. The defects of the photoresist pattern may be inspected based on the weak points in the second reference image when the photoresist pattern on the wafer sample 100 is analyzed.

In step S1000, the weak points of the photoresist pattern caused by an optical proximity correction (OPC) is set up using the weak points of the shot regions 110 in the first portion 130 of the photoresist pattern when the reference exposure condition belongs to the exposure margin of the exposure process.

Figure 6:
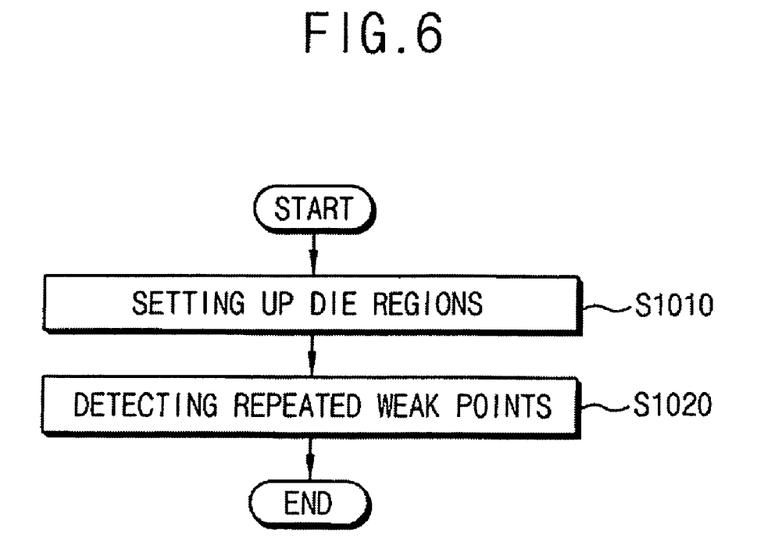
FIG. 6 is a block diagram illustrating a step of setting up weak points of a photoresist pattern caused by an optical proximity correction in accordance with an example embodiment of the present invention.

FIG. 6 is a block diagram illustrating a step of setting up the weak points of the photoresist pattern caused by the optical proximity correction in accordance with example embodiments of the present invention.

Referring to FIGS. 1, 3 and 6, the shot regions 110 of the first portion 130 are divided into a plurality of die regions in step S1010. That is, the die regions are set up in the shot regions 110 of the first portion 130 in step S1010.

In example embodiments, since each of the shot regions 110 of the first portion 130 may be consist of a plurality of die regions, each of the shot regions 110 of the first portion 130 may be divided into the plurality of die regions.

In step S1020, the weak points repeatedly existing in at least two die regions included in each of the shot regions 110 are detected.

Because the weak points repeated in the die regions may be set up as the weak point caused by the optical proximity correction (OPC) of the pattern of the mask. Thus, the pattern of the mask may be corrected using the weak points caused by the optical proximity correction. These weak points caused by the optical proximity correction may be detected with respect to each of the shot regions 110.

In a method of analyzing a wafer sample according to example embodiments of the present invention, after detecting defects of a reference shot region and a shot region adjacent the reference shot region, and defects of a shot region separated form the reference shot region, weak points of a photoresist pattern provided on the wafer sample and a margin of an exposure process may be advantageously set up. Therefore, exposure conditions of the exposure process may be easily set up using the exposure margin, and the wafer sample having the photoresist pattern may be quickly inspected based on the weak points of the photoresist pattern.

The foregoing is illustrative of example embodiments of the present invention and is not to be construed as limiting thereof. Although a few example embodiments of the present invention have been described, those of ordinary skill in the art will readily appreciate that many modifications are possible in the example embodiments without materially departing from the novel teachings and advantages of the present invention. Accordingly, all such modifications are intended to be included within the scope of the present invention as defined in the claims. Therefore, it is to be understood that the foregoing is illustrative of the present invention and is not to be construed as limited to the specific example embodiments disclosed, and that modifications to the disclosed example embodiments, as well as other example embodiments, are intended to be included within the scope of the appended claims. The present invention is defined by the following claims, with equivalents of the claims to be included therein.

What is claimed is:

1. A method of analyzing a wafer sample comprising:
detecting first defects of a photoresist pattern on the wafer sample having a plurality of shot regions exposed by an exposure process with related exposure conditions, respectively, each of the shot region including a first portion exposed within a tolerance error range of a reference exposure condition and a second portion exposed out of the reference exposure condition;
setting up the first defects detected from the second portion of at least two shot regions as second defects of the photoresist pattern;
obtaining a first reference image displaying the second defects;
setting up at least one of the first defects positioned at the first portion of the shot region and corresponding to the second defects of the first reference image as a third defect of the photoresist pattern;
setting up a position of the third defect as a weak point of the photoresist pattern on the first portion of the shot region;

determining the exposure conditions relative to the shot region having no weak point at the first portion thereof as an exposure margin of the exposure process; and obtaining a second reference image displaying the weak point of the photoresist pattern on the first portion of the shot region when the reference exposure condition belongs to the exposure margin of the exposure process.

2. The method of claim 1, further comprising:

setting up a central value of the exposure margin as a new reference exposure condition when the reference exposure condition does not belong to the exposure margin; and analyzing again the wafer sample using the new reference exposure margin.

3. The method of claim 1, further comprising:

reviewing the weak point of the photoresist pattern to identify whether the photoresist pattern actually has the third defect at the weak points before determining the exposure margin of the exposure process.

4. The method of claim 3, wherein reviewing the weak points is performed using a scanning electron microscope.

5. The method of claim 1, further comprising:

correcting the third defect of the photoresist pattern corresponding to the weak point in each of the shot regions of the first portion by performing an optical proximity correction (OPC) process.

6. The method of claim 5, wherein performing the OPC process comprises;

dividing each of the shot regions of the first portion into a plurality of die regions; and detecting the third defect of the photoresist pattern corresponding to the weak point repeatedly existed in at least two of the die regions in each of the shot regions.

7. The method of claim 1, wherein the exposure conditions includes at least two conditions selected from a group consisting of an exposure time, a focal distance, and an exposure intensity.

8. The method of claim 1, wherein detecting the first defect comprises:

preparing the wafer sample having a reference shot region formed by transcribing a predetermined pattern with a reference exposure condition and a peripheral shot region formed by transcribing the predetermined pattern while varying the exposure conditions of the exposure process;

setting up a reference inspection precision using the wafer sample; and inspecting the wafer sample using the reference inspection precision.

9. The method of claim 8, wherein setting up the reference inspection precision comprises:

dividing the wafer sample into a first region having relatively many defects and a second region having relatively few defects;

detecting the defects of the wafer sample by gradually varying an inspection precision;

determining a defect number ratio between the number of defects in the first region and the number of defects in the second region in accordance with the inspection precision; and selecting the reference inspection precision from the inspection precision within a range in which the defect number ratio increases.

10. The method of claim 9, wherein selecting the reference inspection precision comprises:

subtracting a minimum value of the defect number ratio from a maximum value of the defect number ratio within the range in which the defect number ratio increases to obtain a difference between the maximum value and the minimum value;

adding a previously set value of the difference between the maximum value and the minimum value into the minimum value of the defect number ratio, to obtain a sum of the minimum value and the previously set value of the difference; and obtaining the inspection precision corresponding to the sum of the defect number ratio so as to set up the inspection precision as the reference inspection precision.

11. The method of claim 9, wherein selecting the reference inspection precision comprises:

multiplying a difference between inspection precision values by a previously set inspection precision value to obtain an offset value of a previously set inspection precision; and subtracting the offset value from the inspection precision value corresponding to the maximum value of the defect number ratio to obtain the reference inspection precision.

12. The method of claim 8, wherein setting up the reference inspection precision comprises:

obtaining a previously set defect number ratio considering characteristics of the wafer sample;

dividing the wafer sample into a first region having relatively many defects and a second region having relatively few defects;

detecting the defects of the wafer sample by gradually varying the inspection precision;

determining a difference between the number of defects in the first region and the number of defects in the second region in accordance with the inspection precision; and selecting the reference inspection precision from the inspection precision within a range in which the defect number ratio increases.

* * * * *